United States Patent [19]

Dolman et al.

[11] Patent Number: 5,212,197
[45] Date of Patent: May 18, 1993

[54] FUNGICIDALLY ACTIVE PYRAZOLE COMPOUNDS

[75] Inventors: Hendrik Dolman; Johannes Kuipers; Leonarda C. Niemann; Bart Heijne, all of Weesp, Netherlands

[73] Assignee: Duphar International Research B.V., Weesp, Netherlands

[21] Appl. No.: 865,059

[22] Filed: Apr. 8, 1992

[30] Foreign Application Priority Data

Apr. 11, 1991 [EP] European Pat. Off. ........... 91200852

[51] Int. Cl.$^5$ .................. A01N 43/56; A01N 43/653; C07D 403/04
[52] U.S. Cl. .................................. 514/397; 514/383; 548/266.2; 548/312.4
[58] Field of Search ............................ 548/266.2, 336; 514/383, 397

[56] References Cited

U.S. PATENT DOCUMENTS

| | | | |
|---|---|---|---|
| 4,465,680 | 8/1984 | Kraatz | 424/245 |
| 4,803,215 | 2/1989 | Jensen-Korte et al. | 514/407 |
| 4,963,575 | 10/1990 | Buntain et al. | 514/359 |
| 5,032,165 | 7/1991 | Miura et al. | 71/92 |

FOREIGN PATENT DOCUMENTS 2073172 10/1981 United Kingdom .

OTHER PUBLICATIONS

Zeitschrift fur Chemie, vol. 16, No. 10, 1976, pp. 398–399; M. Augustin et al; "Synthese und Reaktivitat von Pyridyl . . .".

Primary Examiner—Patricia L. Morris
Attorney, Agent, or Firm—Stevens, Davis, Miller & Mosher

[57] ABSTRACT

The invention relates to new, fungicidally active pyrazole compounds of the general formula

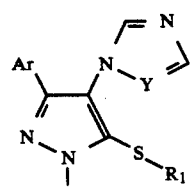

(I)

wherein
Ar is an unsubstituted phenyl group or a phenyl group, substituted with 1 or 2 substituents selected from the group consisting of $C_1$–$C_4$ alkyl, halogen, nitro, cyano and $C_1$–$C_4$ alkoxy, or with 3 halogen atoms,
R is a $C_1$–$C_{12}$ alkyl group,
$R_1$ is a $C_1$–$C_4$ alkyl group, and
Y is CH or N.

The invention also relates to new imidazolylvinyldithioacetals, suitable as starting materials for preparing said new pyrazole compounds and also having fungicidal activity.

6 Claims, No Drawings

FUNGICIDALLY ACTIVE PYRAZOLE COMPOUNDS

The invention relates to new pyrazole compounds and to a method of preparing said compounds. The invention further relates to fungicidal compositions comprising the new compounds, and to the use of said compositions in agriculture and horticulture. The invention finally relates to new imidazolylvinyl-dithioacetals to be used for preparing said pyrazole compounds.

Fungicidal resistance is an increasing problem in crop protection. Nearly all classes of modern fungicides, such as benzimidazoles, 2-aminopyrimidines, phenylamides and dicarboximides, have encountered resistance problems. In particular, effective protection of the crop against Botrytis cinerea, a serious pathogenic fungus of widespread occurrence, occasions increasing brain-racking due to resistance, even cross resistance, to various classes of known fungicides. It is therefore of great importance to provide a fungicidally active compound, in particular intended for preventing or controlling Botrytis cinerea, having a chemical structure which differs fundamentally from the known classes of fungicides and consequently probably having a different mode of action.

It has now been found surprisingly that this need can be met with new pyrazole compounds, which according to the present invention are characterized by the general formula

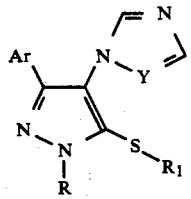

(I)

wherein
Ar is an unsubstituted phenyl group or a phenyl group, substituted with 1 or 2 substituents selected from the group consisting of $C_1$–$C_4$ alkyl, halogen, nitro, cyano and $C_1$–$C_4$ alkoxy, or with 3 halogen atoms,
R is a $C_1$–$C_{12}$ alkyl group,
$R_1$ is a $C_1$–$C_4$ alkyl group, and
Y is CH or N.

The new pyrazole compounds of the present invention are preferably characterized by the general formula

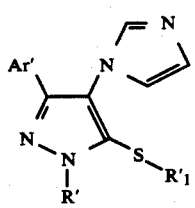

(II)

wherein
Ar' is a phenyl group, substituted with 1–3 halogen atoms,
R' is a $C_1$–$C_6$ alkyl group, and
$R'_1$ is a $C_1$–$C_2$ alkyl group.

It has been observed that the above compounds have a high fungicidal activity, in particular against Botrytis cinerea.

Examples of new pyrazole compounds according to the present invention are:
(1) 1-ethyl-3-(4-chlorophenyl)-4-(1-imidazolyl)-5-methylthio-pyrazole,
(2) 1-n-propyl-3-(4-chlorophenyl)-4-(1-imidazolyl)-5-methylthio-pyrazole,
(3) 1-n-butyl-3-(4-chlorophenyl)-4-(1-imidazolyl)-5-methylthio-pyrazole,
(4) 1-n-pentyl-3-(4-chlorophenyl)-4-(1-imidazolyl)-5-methylthio-pyrazole,
(5) 1-methyl-3-(2,4-dichlorophenyl)-4-(1-imidazolyl)-5-methylthio-pyrazole,
(6) 1-ethyl-3-(2,4-dichlorophenyl)-4-(1-imidazolyl)-5-methylthio-pyrazole,
(7) 1-n-propyl-3-(2,4-dichlorophenyl)-4-(1-imidazolyl)-5-methylthio-pyrazole,
(8) 1-n-butyl-3-(2,4-dichlorophenyl)-4-(1-imidazolyl)-5-methylthio-pyrazole,
(9) 1-n-pentyl-3-(2,4-dichlorophenyl)-4-(1-imidazolyl)-5-methylthio-pyrazole,
(10) 1-n-octyl-3-(2,4-dichlorophenyl)-4-(1-imidazolyl)-5-methylthio-pyrazole,
(11) 1-methyl-3-(3,4-dichlorophenyl)-4-(1-imidazolyl)-5-methylthio-pyrazole,
(12) 1-ethyl-3-(3,4-dichlorophenyl)-4-(1-imidazolyl)-5-methylthio-pyrazole,
(13) 1-n-propyl-3-(3,4-dichlorophenyl)-4-(1-imidazolyl)-5-methylthio-pyrazole,
(14) 1-methyl-3-(2,4,5-trichlorophenyl)-4-(1-imidazolyl)-5-methylthio-pyrazole,
(15) 1-ethyl-3-(2,4,5-trichlorophenyl)-4-(1-imidazolyl)-5-methylthio-pyrazole,
(16) 1-n-propyl-3-(2,4,5-trichlorophenyl)-4-(1-imidazolyl)-5-methylthio-pyrazole,
(17) 1-n-butyl-3-(2,4,5-trichlorophenyl)-4-(1-imidazolyl)-5-methylthio-pyrazole,
(18) 1-ethyl-3-(4-fluorophenyl)-4-(1-imidazolyl)-5-methylthio-pyrazole,
(19) 1-n-propyl-3-(4-fluorophenyl)-4-(1-imidazolyl)-5-methylthio-pyrazole,
(20) 1-ethyl-3-(2,4-difluorophenyl)-4-(1-imidazolyl)-5-methylthio-pyrazole,
(21) 1-n-propyl-3-(3,4-difluorophenyl)-4-(1-imidazolyl)-5-methylthio-pyrazole, and
(22) 1-n-butyl-3-(3,4-difluorophenyl)-4-(1-imidazolyl)-5-methylthio-pyrazole.

The new compounds according to the invention show an interesting fungicidal activity with respect to various pathogenic fungi, which may occur in agricultural and horticultural crops, in particular with respect to the prevention and control of Ascomycetes and Deuteromycetes, for example Botrytis cinerea.

For practical applications the active compounds in accordance with the invention are processed to compositions. In such compositions the active substance is mixed with solid carrier material or dissolved or dispersed in liquid carrier material, if desired in combination with auxiliary substances, for example, emulsifiers, wetting agents, dispersing agents and stabilizers.

Examples of compositions according to the invention are aqueous solutions and dispersions, oily solutions and oily dispersions, solutions in organic solvents, pastes, dusting powders, dispersing powders, miscible oils, granules and pellets.

Dispersible powders, pastes and miscible oils are compositions in concentrate form which are diluted prior to or during use. The solutions in organic solvents are mainly used in air application, namely when large areas are treated with a comparatively small quantity of composition. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/-suspension, if desired in the presence of a binder, on granular carrier material, for example porous granules (sand or ground marlow), organic granules (for example, dried coffee grounds, cut tobacco stems and ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable solvents are, for example, xylene, toluene, petroleum distillates which are rich in aromates, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily water-miscible liquid, for example, a glycol, or glycol ether, to which solution a dispersing agent and, if desired, a surface-active substance has been added. When diluting with water shortly before or during spraying, an aqueous dispersion of the active substance is then obtained.

In addition to the above-mentioned ingredients, the agents according to the invention may also contain other substances known for use in this type of agents. For example, a lubricant, for example, calcium stearate or magnesium stearate, may be added to a dispersible powder or a mixture to be granulated. "Adhesives", for example, polyvinylalcohol cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the invention. As a result of this the activity spectrum of the composition is widened and synergism may occur.

For use in such a combination composition are to be considered known insecticidal, acaricidal and fungicidal compounds, such as the following fungicides.

1. organic tin compounds, for example, triphenyltin hydroxide and triphenyltin acetate;
2. alkylene bisdithiocarbamates, for example, zinc ethylene bisdithiocarbamate and manganese ethylene bisdithiocarbamate;
3. 1-acyl- or 1-carbamoyl-N-benzimidazole(-2) carbamates and 1,2-bis(3-alkoxycarbonyl-2-thiureido)benzene, and furthermore 2,4-dinitro-6-(2-octylphenylcrotonate), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidin-4-yl-dimethylsulphamate, 1-(4-chlorophenoxy)-3,3-dimethyl-1(1,2,4-triazol-1-yl)-2butanone, 1-[2-(2,4-dichlorophenyl)-4-propyl-1,3-dioxolan-2-ylmethyl]-1H-1,2,4-triazole, 2,4'-difluoro-α(1H-1,2,4-triazol-1-ylmethyl)benzhydryl alcohol, α-(2-chlorophenyl)-α(4-fluorophenyl)-5-pyrimidinemethanol, α-(2-clorophenyl)-α(4-chlorophenyl)-5-pyrimidinemethanol, 1-(isopropylcarbamoyl)-3-(3,5-dichlorophenyl)-hydantoin, N-(1,1,2,2-tetrachloroethylthio)-4-cyclohexene-1,2-carboximide, N-trichloromethylthio-4-cyclohexene-1,2-dicarboximide, N-tridecyl-2,6-dimethylmorpholine, and 5,6-dihydro-2-methyl-1,4-oxathiine-3-carboxanilide The dosages of the composition according to the invention desired for practical application will, of course, depend on various factors, for example, field of application, selected active substance, form of composition, nature and extent of the infection and the weather conditions.

In general it holds that favourable results are achieved with a dosage which corresponds to 250–1000 g of the active substance per hectare.

The new pyrazole compounds of the present invention can be prepared by reacting a compound of the general formula

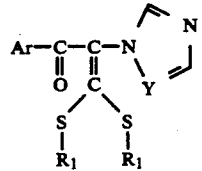

(III)

wherein Ar, $R_1$ and Y have the above meanings, with a compounds of the general formula $$R_3\text{---}NH\text{---}NH_2 \qquad (IV)$$

wherein $R_3$ is a hydrogen atom or a $C_1$–$C_2$ alkyl group. The compound obtained by this reaction, having the general formula

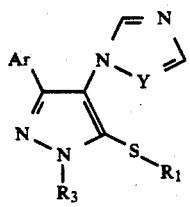
(V)

can then be converted, in case $R_3$ is a hydrogen atom, with a $C_1$–$C_{12}$ alkylating agent, selected from a dialkylsulphate and an alkylhalogenide, preferably an alkyliodide or alkylbromide.

The former reaction, i.e. the ring closure reaction, is preferably carried out in a polar organic solvent, e.g. an alcohol such as ethanol, preferably at elevated temperature, e.g. at reflux temperature, to allow the formed $R_1$SH to escape.

The alkylating reaction can be carried out with an alkyliodide, preferably in the presence of a basic substance, e.g. an alkali metal carbonate or ammonium carbonate. This reaction is preferably performed in a polar organic solvent, e.g. a ketone such as acetone, preferably at a temperature between room temperature and the boiling point of the solvent.

The imidazolylvinyldithioacetals, to be used for the above-described preparation method, are new. Therefore the present invention also relates to these new compounds, which are to be considered as key intermediates in the process for preparing fungicidally active pyrazoles. The new imidazolylvinyldithioacetals of the present invention are characterized by the general formula

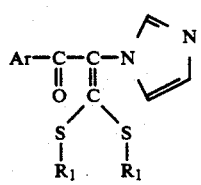
(VI)

wherein Ar and $R_1$ have the above meanings.

It has been found, that also the above compounds of formula VI show an interesting fungicidal activity and are in particular active against Botrytis cinerea. New imidazolylvinyldithioacetals are preferred which have the general formula

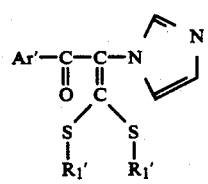
(VII)

wherein Ar' and $R_1'$ also have the above meanings. In this connection reference is made to German patent application ("Offenlegungsschrift") 3145890, wherein chemically related dithioacetals having fungicidal activity are described. As will become apparent from the Examples, however, the tested compounds known from this patent application do not show any fungicidal activity against Botrytis cinerea in practically acceptable dosages.

Examples of such key intermediates according to present invention are:

(a) 1,1-bis(methylthio)-2-(4-chlorobenzoyl)-2-(imidazolyl-1)ethene,
(b) 1,1-bis(methylthio)-2-(2,4-dichlorobenzoyl)-2-(imidazolyl-1)ethene,
(c) 1,1-bis(methylthio)-2-(3,4-dichlorobenzoyl)-2-(imidazolyl-1)ethene,
(d) 1,1-bis(methylthio)-2-(2,4,5-trichlorobenzoyl)-2-(imidazolyl-1)ethene,
(e) 1,1-bis(methylthio)-2-(4-fluorobenzoyl)-2-(imidazolyl-1)ethene,
(f) 1,1-bis(methylthio)-2-(2,4-difluorobenzoyl)-2-(imidazolyl-1)ethene,
(g) 1,1-bis(methylthio)-2-(3,4-difluorobenzoyl)-2-(imidazolyl-1)ethene.

The new imidazolylvinyldithioacetals as defined above can be prepared from the corresponding substituted acetophenones with the general formula

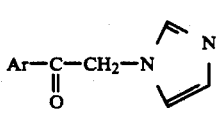
(VIII)

wherein Ar has the above meaning, by successively reacting said acetophenone with carbon disulphide and with a $C_1$–$C_4$ alkylating agent, selected from a dialkylsulphate and an alkylhalogenide, preferably an alkyliodide or alkylbromide.

The reaction with carbon disulphide is preferably carried out in a polar organic solvent, e.g. a dipolar organic solvent such as dimethylformamide, at a slightly reduced temperature. Preferably the reaction product so obtained is directly, i.e without intermediate isolation, converted to the desired dialkyldithioacetal by successive reactions with a suitable basic substance, for example an alkali metal hydride such as sodium hydride, and with an alkylating agent. Suitable alkylating agents are described hereinbefore. Preferred reaction conditions for the alkylation step: polar organic solvent (see above); temperature between approx. 0° C. and the boiling point of the solvent, preferably reduced temperature.

The starting compound for the above reaction, viz. the substituted acetophenone of the general formula VIII, is preferably prepared by reacting the corresponding phenacylhalogenide with imidazole, preferably in a polar organic solvent such as acetonitrile, tetrahydrofurane, dimethylformamide, and the like, at a temperature between 0° C. and the boiling point of the solvent, preferably at reduced temperature. The substituted phenacylhalogenide, e.g. a bromide, required for the above reaction, can easily be prepared by halogenating the corresponding substituted acetophenone, as generally known in the art. The invention will now be described in greater detail with reference to the following specific examples.

EXAMPLE I

Preparing of (3,4-dichlorobenzoyl)imidazolyl-ketenedimethyldithioacetal (c)

(i) Bromine in a quantity of 10.2 ml (0.2 mol) is added dropwise to a mixture of 37.8 g 3.4-dichloroacetophenone and approx. 1.0 g anhydrous $AlCl_3$ in 600 ml dry diethylether while stirring and cooling in ice. After stirring for 0.5 hr at 0° C. and 1.5 hr at room temperature, 30 ml water are added slowly. The organic phase is separated, washed twice with water, dried and evaporated to dryness. A small amount of petroleum ether (40–60) is added to the residue and the mixture is stirred at approx. 0° C. The desired 3.4-dichlorophenacylbromide is obtained as a crystalline material in a yield of 39.8 g (74%); melting point 55°–58° C.; TLC $(CH_2Cl_2)=0.5$.

(ii) To a solution of 39.8 g 3.4-dichlorophenacylbromide, prepared as described sub (i), in 300 ml of acetonitrile are added while stirring and cooling in ice 40.8 g imidazole. After stirring for 2 hours at approx. 0° C. and then another 2 hours at room temperature, the reaction mixture is evaporated to dryness. The residue is dissolved in methylenechloride and water and then sucked off. The organic phase is separated from the filtrate, washed twice with water, dried and evaporated to dryness. The residue is dissolved in methanol and decolourized with charcoal. After evaporation of the solvent the residue is stirred with diethylether. The solid is sucked off and recrystallized from methanol/water. The desired 1-(3,4-dichlorophenacyl)imidazole is obtained in a yield of 22.7 g (60%); m.p. 126°–128° C.; TLC $(CH_3CN)=0.15$.

(iii) To a solution of 21.65 g 1-(3,4-dichlorophenacyl)imidazole, prepared as described sub (ii), in 170 ml dimethylformamide are added while stirring and cooling at 0°–10° C. and under a $N_2$ blanket carbondisulphide in a quantity of 7.65 ml (0.127 mol) and thereupon portionwise 7.65 g (0.17 mol) of a sodiumhydride dispersion. After stirring for 1 hr are added under the same conditions 10.6 ml (0.17 mol) methyliodide. After stirring for another hour, the reaction mixture is poured into icewater; the organic phase is decanted, washed with water and dissolved in methylenechloride.

The solution is then dried and evaporated to dryness. The residue is chromatographed (silicagel/ethylacetate) and the product obtained is again dissolved in methylenechloride. After filtration this solution is diluted with diisopropylether and the methylenechloride is evaporated. The desired crystalline title compound (c) is sucked off; yield 73%; m.p. 92° C.

In a corresponding manner the following compounds are prepared; the letters correspond with the reference letters used before in the description.

| compound | melting point |
| --- | --- |
| (a) | 94° C. |
| (b) | 95° C. |
| (d) | 154° C. |
| (e) | 71° C. |
| (f) | oil |
| (g) | 83° C. |

EXAMPLE II

Preparation of 1-methyl-3-(3,4-dichlorophenyl)-4-(1-imidazolyl)-5-methylthio-pyrazole (11)

To a solution of 3.59 g (0.01 mol) of (3,4-dichlorobenzoyl)imidazolyl-dimethyldithioacetal, prepared as described in Example I, in 40 ml of abs. ethanol is added 0.52 ml (0.01 mol) of methylhydrazine. The reaction mixture is stirred for one hour at room temperature and then for one hour under reflux. The solvent is evaporated and the residue is dissolved in methylenechloride. The solution is dried, partly evaporated and diluted with diisopropylether. After decolourizing with charcoal the solvents are evaporated to dryness and the residue is chromatographed (silicagel/ethyl-acetate). The isolated product is recrystallized from diisopropylether. The title compound is obtained in a yield of 1.15 g; m.p. 88°–90° C., TLC (EtOAc)=0.35. The structure is confirmed by NMR.

In a corresponding manner the following compounds are prepared; the numbers correspond with the reference number used before in the description.

| compound | physical data |
| --- | --- |
| (1) | m.p. 116° C. |
| (5) | m.p. 107°C. |
| (6) | m.p. 99° C. |
| (12) | m.p. 118° C. |
| (14) | m.p. 104° C. |
| (15) | m.p. 102° C. |
| (18) | m.p. 91° C. |
| (20) | oil; $^1$H-NMR(CDCl$_3$): δ 1.46(t.3H); 2.08(s.3H); 4.37(q.2H); 6.72(m.1H); 6.83(m.1H); 6.90(s.1H); 7.07(s.1H); 7.30(m.1H); 7.45(s.1H). |

EXAMPLE III

Preparation of 1-n-propyl-3-(3,4-dichlorophenyl)-4-(1-imidazolyl)-5-methylthio-pyrazole (13)

(i) To a solution of 10.77 g (0.03 mol) of (3,4-dichlorobenzoyl)imidazolyl-dimethyldithioacetal, prepared as described in Example I, in 120 ml of abs. ethanol is added 1.5 ml hydrazinehydrate. The reaction mixture is stirred for one hour at room temp. and then for another hour under reflux. The excaping methanethiol is received in bromine/ methylenechloride. After evaporation the residue is refluxed in acetonitrile. After cooling down to room temperature the desired 3-(3,4-dichlorophenyl)-4-(1-imidazolyl)-5-methylthiopyrazole is obtained in a yield of 8.19 g. This product can be purified by recrystallization from acetone: m.p. 217°–220° C.; TLC $(CH_3CN)=0.4$.

(ii) The above product is alkylated in the 1-position by dissolving 3.25 g together with 2.76 g $K_2CO_3$ and 1.0 ml of n-propyliodide in 50 ml acetone. After reflux for 4 hours and cooling down to room temp., the precipitate is sucked off and washed with acetone. The combined organic solutions are evaporated to dryness. The residue is chromatographed (silicagel; ethyl acetate). The isolated product is recrystallized from diisopropylether, yielding 1.89 g of the title compound (13); m.p. 91°–93° C. TLC (EtOAc)=0.35. The structure is confirmed by NMR.

In a corresponding manner the following compounds are prepared; the numbers correspond with the reference number used before in the description.

| compound | physical data |
|---|---|
| (2) | m.p. 82° C. |
| (3) | m.p. 61° C. |
| (4) | oil; $^{13}$C-NMR(CDCl$_3$): δ 13.92(q); 18.72(q); 22.22(t); 28.71(t); 30.11(t); 50.36(t); 120.30(s); 121.01(d); 127.49(2d); 128.82(2d); 129.42(s); 130.09(d); 133.14(s); 134.12(s); 138.37(d); 144.26(s). |
| (7) | oil; $^{13}$C-NMR(CDCl$_3$): δ 11.10(q); 18.52(q); 23.75(t); 51.93(t); 120.07(d); 122.14(s); 127.33(d); 128.83(s); 129.35(d); 129.66(d); 130.83(s); 132.51(d); 134.76(s); 135.47(s); 137.59(d); 142.64(s). |
| (8) | oil; $^{13}$C-NMR(CDCl$_3$): δ 13.66(q); 18.51(q); 19.80(t); 32.41(t); 50.19(t); 120.05(d); 122.15(s); 127.24(d); 128.87(s); 129.42(d); 129.66(d); 130.71(s); 132.53(d); 134.76(s); 135.44(s); 137.59(d); 142.61(s). |
| (9) | oil; $^{13}$C-NMR(CDCl$_3$): δ 13.92(q); 18.52(q); 22.20(t); 28.68(t); 30.08(t); 50.46(t); 120.04(d); 122.17(s); 127.23(d); 128.87(s); 129.46(d); 129.69(d); 130.70(s); 132.51(d); 134.80(s); 135.47(d); 137.61(d); 142.64(s). |
| (10) | oil; $^{13}$C-NMR(CDCl$_3$): δ 14.08(q); 18.55(q); 22.62(t); 26.58(t); 29.09(t); 29.12(t); 30.44(t); 31.74(t); 50.55(t); 120.08(d); 122.18(s); 127.28(d); 128.84(s); 129.46(d); 129.77(d); 130.73(s); 132.48(d); 134.84(s); 135.57(s); 137.65(d); 142.71(s). |
| (16) | m.p. 99° C. |
| (17) | oil; $^{13}$C-NMR(CDCl$_3$): δ 13.66(q); 18.50(q); 19.85(t); 32.43 (t); 50.34(t); 119.97(d); 122.27(s); 129.68(d); 130.29(s); |
| (17) | 130.98(s); 131.13(d); 131.32(s); 132.79(s); 132.84(d); 133.83(s); 137.58(d); 141.68(s). |
| (19) | m.p. 119° C. |
| (21) | m.p. 80° C. |
| (22) | oil; $^{13}$C-NMR(CDCl$_3$): δ 13.68(q); 18.75(q); 19.90(t); 32.50(t); 50.24(t); 115.48(d); 117.61(d); 120.28(s); 121.00(d); 122.32(d); 127.99(s); 130.36(d); 133.51 (s); 138.44(d); 143.63(s); 150.38(s); 150.49(s). |

EXAMPLE IV (i) Preparation of a solution of an active substance, viz. 1-ethyl-3-(2,4-dichlorophenyl)-4-(1-imidazolyl)-5-methylthiopyrazole (6), in a water-miscible liquid ("liquid").

10 g of the above active substance are dissolved in a mixture of 10 ml of isophorone and approx. 70 ml of dimethylformamide, after which polyoxyethylene glycol ricinyl ether as an emulsifier is added in a quantity of 10 g.

The other active substances are processed in a corresponding manner to 10 or 20% "liquids".

In a corresponding manner, "liquids" are obtained in N-methyl pyrrolidone, dimethyl formamide, and a mixture of N-methyl pyrrolidone and isophorone as solvents.

(ii) Preparation of a solution of the active substance in an organic solvent.

200 mg of the active substance to be investigated are dissolved in 1,000 ml of acetone in the presence of 1.6 g of nonylphenol polyoxyethylene. After pouring in water, this solution can be used as a spraying liquid (iii) Preparation of an emulsifiable concentrate of the active substance.

10 g of the active substance to be investigated are dissolved in a mixture of 15 ml of isophorone and 70 ml of xylene; 5 g of a mixture of a polyoxyethylene sorbitan ester and an alkylbenzene sulphonate are added to this solution as an emulsifier.

(iv) Preparation of a dispersible powder (W.P.) of the active substance.

25 g of the active substance to be investigated are mixed with 68 g of kaolin in the presence of 2 g of sodium butyl naphthalene sulphonate and 5 g of lignine sulphonate.

(v) Preparation of a suspension concentrate (flowable) of the active substance.

A mixture of 10 g of active substance, 2 g of lignine sulphonate, and 0.8 g of sodium alkyl sulphate is supplied with water to a total quantity of 100 ml.

(vi) Preparation of a granule of the active substance.

7.5 g of active substance, 5 g of sulphite lye, and 87.5 g of ground dolomite are mixed, after which the resulting mixture is processed to a granular composition by means of the so-called compacting method.

EXAMPLE V

In vitro test on activity against Botrytis cinerea

The compound to be tested is processed in a culture medium consisting of 1% by weight of glucose, 0.2% by weight of a 5 yeast extract (marmite), 0.5% by weight of a protein (pepton), 2.5% by weight of agar-agar, and 95.8% by weight of water, in petri dishes in a concentration of 30 ppm The petri dishes are inoculated with the plant-pathogenic fungus Botrytis cinerea and then kept at a temperature of 20° C. After 48 hours the growth-inhibiting activity of the compounds is determined visually. In Table A below the inhibition of the mycelium growth is recorded, compared to the control (untreated). The reference numerals correspond again with the numbers used before.

TABLE A

| compound no | % growth inhib. |
|---|---|
| (1) | 78 |
| (2) | 82 |
| (3) | 67 |
| (4) | 58 |
| (5) | 89 |
| (6) | 96 |
| (7) | 100 |
| (8) | 73 |
| (9) | 73 |
| (12) | 66 |
| (13) | 63 |
| (14) | 55 |
| (15) | 67 |
| (16) | 68 |
| (17) | 67 |
| (18) | 53 |
| (19) | 68 |
| (20) | 93 |
| (21) | 70 |
| (22) | 67 |

EXAMPLE VI

Test with respect to the protection of seedlings against Botrytis cinerea

The compounds to be tested are processed to spray liquids, as described in Example IV (ii), in a concentration of 300 ppm. Zinnia seedlings having one pair of leaves are treated with the spray liquids by using a conventional sprayer. Four hours after application the inoculation is performed by using agar disks of 4 mm diameter in which germinated spores of Botrytis cinerea are dispersed and which are placed on the leaves. After inoculation the plants are kept at 19° C. in a humid cabinet which is placed on a glass house bench and which is cooled with well water. After approx. 4 days assessment is performed by estimating the disease incidence per leaf using a score index ranging from 0 to 3. The disease ratings are totalized per plant and per treatment and expressed in percentages of the sum of an equal number of untreated check plants.

The percentage diseased plants is recorded in Table B below; the reference numerals correspond again with the numbers used in the specification.

TABLE B

| compound no. | percentage diseased plants |
|---|---|
| (1) | 0-10 |
| (2) | 0-10 |
| (5) | 0-10 |
| (6) | 0-10 |
| (7) | 0-10 |
| (8) | 0-10 |
| (14) | 0-10 |
| (16) | 0-10 |
| (20) | 0-10 |
| (a) | 10-25 |
| (b) | 0-10 |
| (e) | 0-10 |
| — (control) | 100 |

In the same test the following known compounds are tested by comparison:
1,1-bis(isopropylthio)-2-(4-chlorobenzolyl)-2-(triazolyl-1)ethene;
1-bis(methylthio)-2-benzoyl-2-(triazolyl-1)ethene;
1,1-bis(4-chlorobenzylthio)-2-benzoyl-2-(imidazolyl-1)ethene; and
1,1-bis(propargylthio)-2-benzoyl-2-(imidazolyl-1)ethene.

The above four compounds did not show any activity against Botrytis cinerea; test concentration 300 ppm.

We claim:

1. Pyrazole compound of the formula

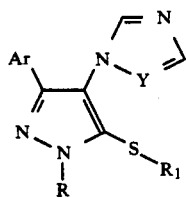

(I)

wherein
Ar is an unsubstituted phenyl group or a phenyl group, substituted with 1 or 2 substituents selected from the group consisting of $C_1$–$C_4$ alkyl, halogen, nitro, cyano and $C_1$–$C_4$ alkoxy, or with 3 halogen atoms,
R is a $C_1$–$C_{12}$ alkyl group,
$R_1$ is a $C_1$–$C_4$ alkyl group, and
Y is CH or N.

2. Compound as claimed in claim 1, having the formula

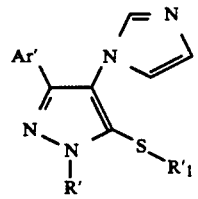

(II)

wherein
Ar' is a phenyl group, substituted with 1–3 halogen atoms,
R' is a $C_1$–$C_6$ alkyl group, and
$R'_1$ is a $C_1$–$C_2$ alkyl group.

3. A fungicidal composition, characterized in that the composition, in addition to a liquid or solid carrier material and, if desired, inert auxiliary substances selected from the group consisting of emulsifiers, wetting agent, dispersing agents and stabilizers, comprises in a fungicidally effective quantity a compound of the formula I, shown in claim 1, wherein the symbols Ar, R, $R_1$ and Y have the meanings given in claim 1.

4. A fungicidal composition characterized in that composition, in addition to a liquid or solid carrier material and, if desired, inert auxiliary substances selected from the group consisting of emulsifiers, wetting agents, dispersing agents and stabilizers has as active ingredient a fungicidally effective amount of a compound of the formula II, wherein Ar' is a phenyl group substituted with 1–3 halogen atoms, and $R'_1$ is a $C_1$–$C_2$ alkyl group.

5. A method of preventing or controlling fungus infections in agriculture and horticulture, characterized in that the infected crop or the crop to be protected is treated with a fungicidal composition as claimed in claim 3 in a dosage from 250 to 1000 g of active substance per hectare.

6. A method of preventing or controlling fungus infections in agriculture and horticulture, characterized in that the infected crop or the crop to be protected is treated with a fungicidal composition as claimed in claim 4 in a dosage of from 250 to 1000 g of active substance per hectare.

* * * * *